United States Patent
Bonne et al.

(10) Patent No.: US 7,401,497 B2
(45) Date of Patent: Jul. 22, 2008

(54) MICRODISCHARGE DETECTOR METHOD AND APPARATUS

(75) Inventors: Ulrich Bonne, Hopkins, MN (US); Teresa M. Marta, White Bear Lake, MN (US); Fouad Nusseibeh, Champlin, MN (US)

(73) Assignee: Honeywell International Inc., Morristown, NJ (US)

( * ) Notice: Subject to any disclaimer, the term of this patent is extended or adjusted under 35 U.S.C. 154(b) by 187 days.

(21) Appl. No.: 11/262,901

(22) Filed: Oct. 31, 2005

(65) Prior Publication Data

US 2007/0095125 A1    May 3, 2007

(51) Int. Cl.
*G01N 30/64* (2006.01)
*G01N 30/78* (2006.01)
*G01N 27/68* (2006.01)

(52) U.S. Cl. .................. 73/23.35; 73/23.4; 73/23.41
(58) Field of Classification Search ............ 73/23.35, 73/23.4, 23.41
See application file for complete search history.

(56) References Cited

U.S. PATENT DOCUMENTS

| | | | |
|---|---|---|---|
| 3,540,851 | A | 11/1970 | Vree et al. |
| 4,054,384 | A | 10/1977 | Hawes |
| 5,166,755 | A | 11/1992 | Gat |
| 2005/0142662 | A1 | 6/2005 | Bonne |
| 2005/0148270 | A1 | 7/2005 | Eden et al. |

FOREIGN PATENT DOCUMENTS

| | | | |
|---|---|---|---|
| GB | 2344212 | 5/2000 | |
| KR | 2004-37978 A | * 5/2004 | ................ 73/23.35 |
| WO | WO-0244698 A1 | 6/2002 | |
| WO | WO-2005066620 A1 | 7/2005 | |

OTHER PUBLICATIONS

"Microdischarge Arrays: A New Family of Photonic Devices (Revised*)" S.-J. Park et al. IEEE Journal on Selected Topics in Quantum Electronics, vol. 8, No. 2, Mar./Apr. 2002, pp. 387-394.
"Arrays of Silicon Microdischarge Devices with Multicomponent Dielectrics" S.-J. Park et al. Optic Letters, vol. 26, No. 22, Nov. 15, 2001, pp. 1773-1775.
"Photodetection in the Visible, Ultraviolet, and Near-Infrared with Silicon Microdischarge Devices" S.-J. Park et al. Applied Physics Letters vol. 81, No. 24, Dec. 9, 2002, pp. 4529-4531.
Home page of OceanOptics.com dated Feb. 22, 2006.

* cited by examiner

*Primary Examiner*—Daniel S Larkin
(74) *Attorney, Agent, or Firm*—Kris T. Fredrick

(57) ABSTRACT

A differential microdischarge detector system. The system comprises two microdischarge detectors (MDDs). One of the MDDs is connected to receive sample analytes to be measured, while the other MDD is connected to receive a reference sample that contains interfering gases and none or a much lower concentration of the sample analytes to be measured. The outputs of the two MDD's are fed to a circuit that generates either a difference or a ratio between the measurements of the two MDDs. In addition, the current, impedance or voltage across the electrodes of the two MDDs may be measured and processed to generate either a difference or a ratio signal, thus obtaining additional information about the sample gas analytes.

24 Claims, 3 Drawing Sheets

MICRODISCHARGE DETECTOR METHOD AND APPARATUS

FIELD OF THE INVENTION

The invention pertains to microdischarge detectors that can be employed, for instance, as stand-alone sensors or as detectors in gas chromatographs.

BACKGROUND OF THE INVENTION

Microdischarge detectors (MDDs) or sensors may be used for detecting the presence of molecules in a gas sample on the basis of their optical emission spectrum as excited and emitted by that discharge.

A microdischarge detector comprises a chamber within which a sample (e.g., a gaseous or vapor fluid) is introduced so as to flow between two closely spaced electrodes. The electrodes typically might be spaced on the order of 20-200μ apart. A voltage is generated across the electrodes so as to cause an electrical discharge between the electrodes. Typical voltages for a microdischarge detector might be on the order of 200-600 Volts. This voltage and associated current could be continuous (i.e., DC) or alternating AC. As the sample fluid passes between the electrodes and gets hit by the electrical discharge, the elemental components of the fluid will emit electromagnetic waves. Every element has a characteristic emission spectrum or signature spectrum. One or more photodetectors detect the emission spectrum. Typically, the microdischarge detector will have an array of photodiodes, each photodetector filtered to receive a different, narrow bandwidth of radiation. The emission spectrum can then be analyzed to determine what element or elements comprise the sample.

One particular scientific measurement instrument in which a microdischarge detector is used is a gas chromatograph (GC). In a gas chromatograph, a sample pulse of gas is introduced into a carrier stream of another gas. The carrier stream typically comprises helium, hydrogen, or nitrogen. However, other carrier gases, such as air (environmental or a patient's breath) may also serve as a carrier gas, especially in a micro gas chromatograph, such as PHASED (see, e.g., U.S. Pat. No. 6,393,894).

A pump pushes or pulls the carrier gas through a tortuous capillary path containing a polymer that adsorbs and desorbs the molecules of the gases. The polymer, for instance, may be a coating on the internal walls of the capillary path. The sample gas whose composition is to be determined is introduced as a pulse into the carrier gas at the inlet to the capillary path. The polymer coating adsorbs and desorbs the molecules in the gas mixture (including the molecules of the carrier gas as well as the molecules of the sample pulse gas). The heavier the molecule within the mixture, the more slowly is it adsorbed and desorbed. Accordingly, the heavier the molecule, the longer it will take to pass through the capillary from the inlet to the outlet. The outlet of the capillary is connected to a microdischarge detector. The microdischarge detector, therefore, detects not only the electromagnetic emission spectrum as peaks pass through the electrodes, but also the time at which the peak passes through the electrodes. Accordingly, the output information from the microdischarge detector provides two dimensions of data that can be used to determine what atoms and/or molecules are in the sample gas, namely, 1) the time delay through the capillary for each peak, and 2) the emission spectrum of each peak.

Since polymer adsorbs and desorbs the carrier gas also, the signature emission spectrum of the carrier gas also is detected by the microdischarge detector. This background signal, i.e., the electromagnetic emission lines/bands and/or electrical plasma properties of the carrier gas essentially constitute interference with the measurement of the analytes to be detected and carried by the sample gas. This is particularly problematic if the carrier or sample gas is air since air is a mixture containing $N_2$, $O_2$, $H_2O$, Ar, $CO_2$, $NO_x$ and additional trace gases, all of which have emission spectra. The emission bands of all of these molecules may mask the sample gas microdischarge emission properties and "signatures" of the analytes of interest. They also can change as a function of pressure, time and temperature, further diminishing the ability to obtain an accurate measurement.

Conventionally, zero spectral emission between the active emission bands is used as a reference baseline in spectrometers. As an improvement of that, commercial spectrometers, such as those by Ocen Optics, provide means for subtracting the carrier gas spectrum from the sample gas or peak-gas emission spectrum, to better visualize and measure the bands of interest. However, such spectrometers record the two spectra sequentially in time before subtracting one from the other.

Accordingly, it is an object of the present invention to provide an improved microdischarge detector system.

It is another object of the present invention to provide an improved gas chromatograph.

SUMMARY OF THE INVENTION

The invention is a differential microdischarge detector system. The system comprises two microdischarge detectors (MDDs) with output measurement signals that are combined to generate a differential measurement signal with reduced or eliminated noise components. If employed in connection with a gas chromatograph, for instance, one of the MDDs is connected to receive the gas sample to be measured (including the carrier gas) after it has passed through and been separated into its individual components by the gas chromatograph. The sample to be measured is the series of peaks representing the separated analytes, which elute from the outlet of the polymer-coated capillary. Each of the eluting peaks, when entering the discharge space, emits an optical-spectral emission that is characteristic of its molecular composition, together with that of the carrier gas. The other MDD is connected to receive a reference gas sample. The reference sample may be the carrier gas without the sample pulse. However, it may also be the carrier gas containing the to-be-analyzed sample gases, but in an un-pre-concentrated and un-separated state. The reference sample has an emission spectrum that may interfere with or mask the spectral emission to be measured.

The outputs of the two MDD's are fed to a differential circuit that outputs the difference or ratio between the signals from the two MDDs, thereby suppressing or effectively eliminating the interference signals of the carrier gas from the measurements of the sample gas pulse.

In addition, in a preferred embodiment of the invention, the current, impedance, or voltage across the electrodes of the two MDDs are input to another differential circuit and the differential signal obtained therefrom is taken as a third dimension measurement providing even more information about the sample gas.

The temperature, time-dependent composition, and pressure of a gas, as well as the velocity across the electrodes all have a bearing on the emission spectrum of that gas. Accordingly, in a preferred embodiment of the invention, the MDD chambers are designed relative to each other to assure that the pressure, time, temperature, and velocity of the gasses in those chambers are equal to each other.

The time issue is resolved in a preferred embodiment of the invention, by selecting the path of the gas to the reference MDD such that that the delay through it is equal to the delay through the capillary of the gas chromatograph. This is desirable because the carrier gas may not have uniform composition over time and thus, in order to assure as accurate results as possible, it is advantageous to assure that the portions of the carrier gas passing through the electrodes of the two MDDs are as close in time from the original carrier gas source as possible.

DETAILED DESCRIPTION OF THE INVENTION

Figure 1:
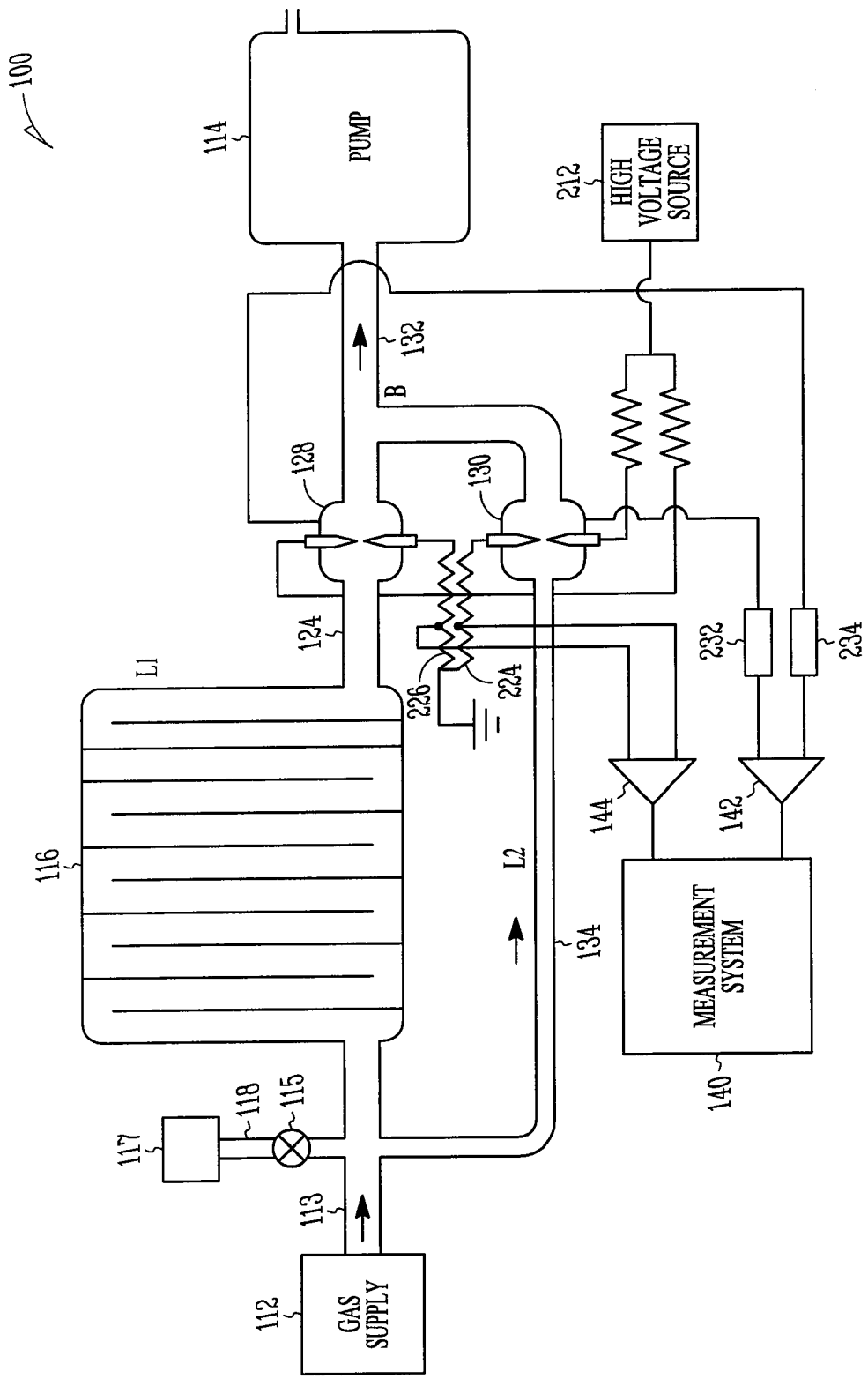
FIG. 1 is a schematic diagram of a gas chromatograph incorporating an embodiment of the present invention.

FIG. 1 is a schematic diagram of a gas chromatograph system 100 employing a microdischarge detection system in accordance with one particular embodiment of the present invention. A carrier gas supply 112 supplies a carrier gas, such as air, hydrogen, or helium, to the system through an input conduit 113. A pump 114 draws the carrier gas through the system. The pump is shown at the end of the system, pulling the gas through the system. However, it could just as easily to be at the beginning of the system pushing the carrier gas through the system. The polymer coated capillary of the gas chromatograph is shown at 116. A sample gas supply 117 is coupled via a conduit 118 to introduce millisecond-wide pulses of the sample gas into carrier stream in the input conduit 113 at or near the inlet to the capillary 116 by means of opening valve 115 for a few milliseconds. Other means that can be used to provide such sample gas pulses, such as via preconcentrator injection pulses as described in U.S. Pat. No. 6,393,894. The outlet of the capillary 116 is coupled via another conduit 124 to the inlet of a first microdischarge detector 128. The outlet of the microdischarge detector is coupled by another conduit 132 to the pump 114.

A bypass conduit 134 is coupled to the input conduit 113 just prior to the sample gas input conduit 118. The bypass conduit is not coated with the polymer in capillary 116. Bypass conduit 134 has an outlet coupled to the inlet of a second microdischarge detector 130. The outlet of the second microdischarge detector 130 is coupled into the output conduit 132.

Each MDD 128, 130 provides two measurement signals of interest. The first is the output of the photodetectors from which the emission spectrum of the gases passing through the electrodes can be determined. The second is the current through the electrodes. As previously noted, the first measurement signal contains two different forms of information, namely, 1) the spectral information itself and 2) the timing of the spectral peaks.

Since the effect of the carrier gas on the measurement signals output by the first MDD 128 essentially constitutes interference with the desired measurements of the analytes of the sample gas, it would be desirable to either subtract the measurement data that is caused by a carrier gas from the output signals of the first MDD 128, or ratio out such reference gas signature. It should be clear that the gas flowing through the first MDD 128 includes the sample pulse as well as the carrier gas, whereas the gas flowing through the second MDD 130 contains the carrier gas without the analyte gases or only a dilute, unseparated concentration of them.

Thus, the output signals of the photodetectors of the first MDD 128 and the output signals of the photodetectors of the second MDD 130 are input to a differential circuit 142, which generates at its output a difference or ratio between the output signals of the first and second MDDs 128, 130. Although shown as a single line in the drawing for each MDD, it will be understood by those of skill in the art that the outputs of the photodetectors of each of the MDDs actually may comprise several hundred distinct outputs (i.e., one from each photodetector that detects a different narrow bandwidth). The output signal of the differential circuit essentially comprises the emission spectrum of the sample gas with the spectrum of the carrier gas eliminated or suppressed since the differential circuit essentially cancelled out the emission spectrum of the carrier gas.

The differential circuits 142 and 144 in the figures are intended to be illustrative of a function performed in accordance with the principles of the present invention, and not limiting. The term differential circuit is used in this specification and claims to refer to any circuitry that can generate the difference or ratio between two input signals. It should be understood that the function of generating the difference or ratio of the two measurement signals can be performed by any suitable analog or digital circuitry, including a differential operational amplifier, a digital processor, a properly programmed general purpose computer, a state machine, suitable analog circuitry, an ASIC, etc. Also, the terms differentiate, differential and all of their other forms is used herein to generally mean the difference between two signals or the ratio of two signals. This is not to preclude the possibility that more complex polynomial or arithmetic functions of the two signals can be developed that factors out noise from the carrier gas, noise from differences in the environmental conditions of the two gasses (e.g., pressure, temperature, velocity), differences in the circuitry of the two MDDs and/or other sources of error in the measurement signals.

The output signals from the differential circuit 142 are provided to a measurement system 140 for analysis of the composition of the sample gas pulse. The measurement system might be a computer or microprocessor appropriately programmed to analyze the spectra to determine the composition of the gas.

The impedance across the gap between the electrodes of each MDD is affected by the composition of the gas between the two electrodes. Thus, the current and voltage across through the electrodes will be affected by the composition of the gas passing between the electrodes of the MDD. Hence, in a preferred embodiment of the invention, the current, voltage, and/or impedance across the electrodes of the first and second MDDs also are input to a second differential circuit 230, which generates an output signal that is the difference or ratio between the two. The differential signal between the two MDDs is taken and analyzed by a measurement system 140 to provide additional useful information about the sample gas. The measurement of the current passing through the electrodes as sample pulses pass through the electrodes can provide additional information about the identity (via the elution time) and composition (via the current amplitude in relation to the optical output) of the sample gas.

Figure 2:
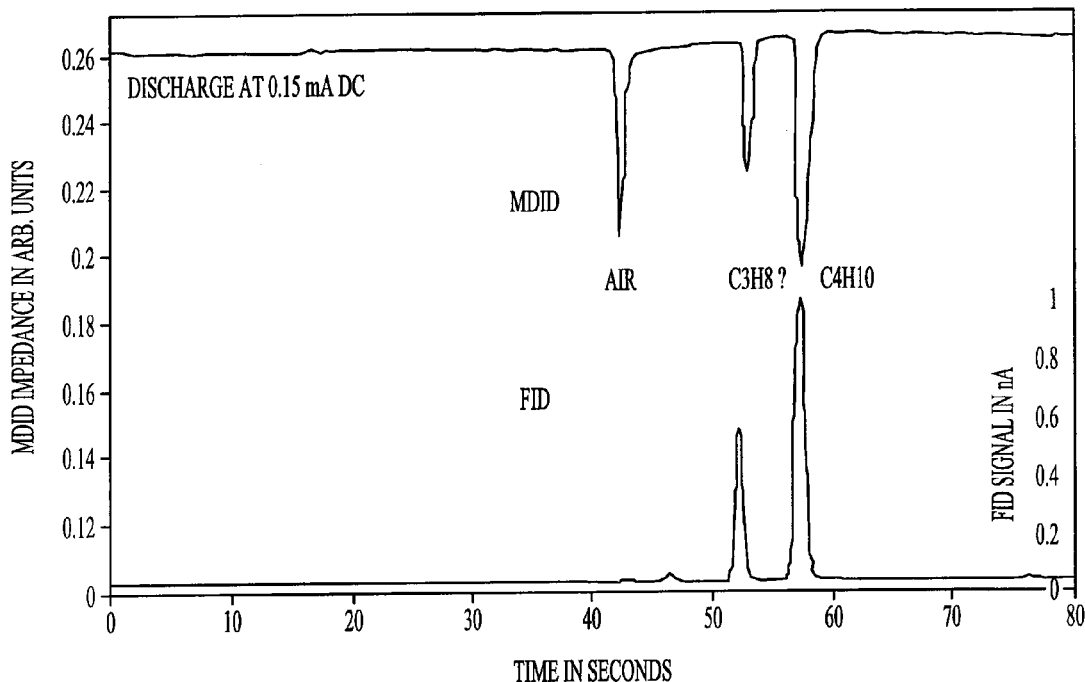
FIG. 2 is a graph illustrating changes in impedance as the peaks of air, propane and butane elute from a conventional, non-differential microdischarge (ionization) detector (MDID), relative to the changes in impedance that would be detected in a traditional Flame Ionization Detector (FID).

FIG. 2, for example, shows a comparison of the impedance changes as the peaks of air, propane and butane contained in a helium carrier gas elute for a conventional, non-differential MDD, relative to the changes in impedance that would be detected in a traditional Flame Ionization Detector (FID). Plotting either the voltage or the current across the electrodes of the MDD would provide essentially the same information as plotting impedance. The current, voltage, or impedance measurements from the MDD provide essentially the same information as the FID instrument. In fact, it provides even more useful information since the MDD current/voltage/impedance is responsive to air, whereas air is undetectable by an FID instrument. This information is in addition to the spectral emission data obtained from the optical detection system. Note that the spectral emission data at the air, propane and butane elution times would simultaneously include spectral emissions caused by N2, O2, CH, and $C_2$ molecules in the injected gas mixture pulse.

Figure 3:
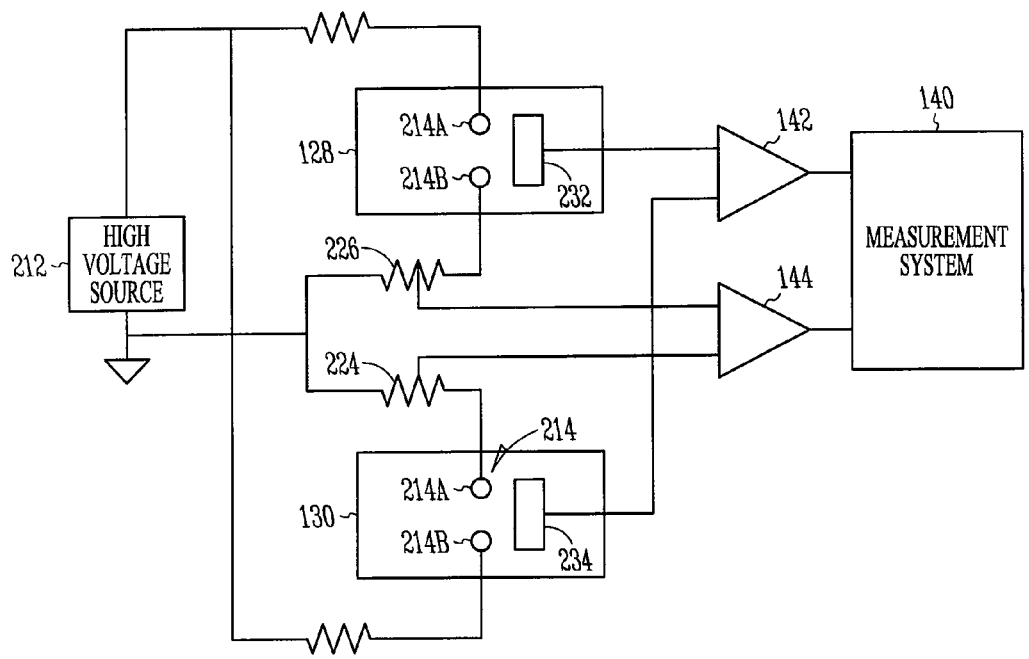
FIG. 3 is a more detailed schematic diagram of the microdischarge detectors and subsequent circuitry of FIG. 1.

FIG. 3 is a schematic diagram illustrating the structure of the MDDs 128, 130 and subsequent circuitry of FIG. 1 in more detail. As shown in FIG. 3, a high voltage source 212 supplies a voltage across the electrodes 214a, 214b and 216a, 216b, respectively, of the first and second microdischarge detectors 128 and 130. Current through the electrodes is tapped via variable resistors 244 and 246 and input to the input terminals of a differential circuit 144. The output signal of the differential circuit 144 is input to the measurement system 150. Likewise, the output of the photodetector arrays 252 and 254 of the microdischarge detectors 128, 130, respectively, are input, via optical fibers, for instance, to the input terminals of the other differential circuit 142. This differential output is fed to the measurement system 150.

Using the differential signals between the output of the gas chromatograph and the output of the bypass path (current and/or optical) eliminates or minimizes the noise/interference signals caused by the carrier gas.

Since the temperature and pressure of the gas as well as its velocity past the electrodes of the MDDs all affect the emission spectra of the gas, it is desirable to assure that the pressure, temperature and velocity in the chambers of the two MDDs are identical. Also, it is desirable to assure that the time delays of the gasses through the two alternate paths to the first and second MDDs, respectively, are equal in order to minimize or eliminate any errors caused by any variations in the composition of the carrier gas at different points in the carrier gas stream.

Accordingly, the diameter and length of the bypass conduit should be selected to so as to assure that the delay through the bypass conduit 134 is equal to the delay through the gas chromatograph 116. An appropriate length and diameter can be calculated as shown below.

If $L_1$=length of path through gas chromatograph capillary to MDD 128

$L_2$=length of alternate path through bypass conduit to MDD 130;

$r_1$=radius of gas chromatograph capillary;
$r_2$=radius of bypass conduit;
$t_1$=time delay of gas through gas chromatograph path;
$t_2$=time delay of gas through bypass path;
$V_1$=volume of chamber of first MDD 128;
$V_2$=volume of chamber of second MDD 130;
$V^*_1$=flow rate of gas through first MDD 128;
$V^*_2$=flow rate of gas through second MDD 130;
$v_1$=velocity of gas through first MDD 128;
$v_2$=velocity of gas through second MDD 130;
$s_1$=cross-section of chamber of first MDD 128; and
$s_2$=cross-section of chamber of second MDD 130, then $$t_1 = V_1/V^*_1 \cong L_1^2/r_1^2 \text{ and}$$

$$t_2 = V_2/V^*_2 \cong L_2^2/r_2^2.$$

Since we want $t_1=t_2$ or $t_1/t_2=1$, we have $$(L_1^2/R_1^2)/(L_2^2/r_2^2)=1 \text{ or}$$

$$(L_1 r_2)/(L_2 r_1)=1$$

It is a simple matter to select the length $L_2$ and the radius $r_2$ of the bypass conduit relative to the length $L_1$ and radius roof the capillary accordingly.

We also would like to set the gas flow velocities through each of the MDD chambers equal. Thus, we set the ratio $$v_1/v_2=1$$

This condition is met if $$L_1/L_2 = s_1/s_2.$$

Thus, merely as an example, if we had selected bypass conduit dimensions such that $L_1/L_2=5$ and $r_1/r_2=5$ (in order to set $t_1=t_2$), then the cross section of the chambers of the two MDDs must be set to the same ratio, i.e., $s_1/s_2=5$.

Furthermore, we can set the pressure differential between the inputs and the outputs of the two paths substantially equal by connecting the two conduits at 142 as shown in FIG. 1.

The present invention is counterintuitive because spectral emission sensors such as those in the MDD's, are generally assumed to be well referenced to zero emission.

Figure 4A:
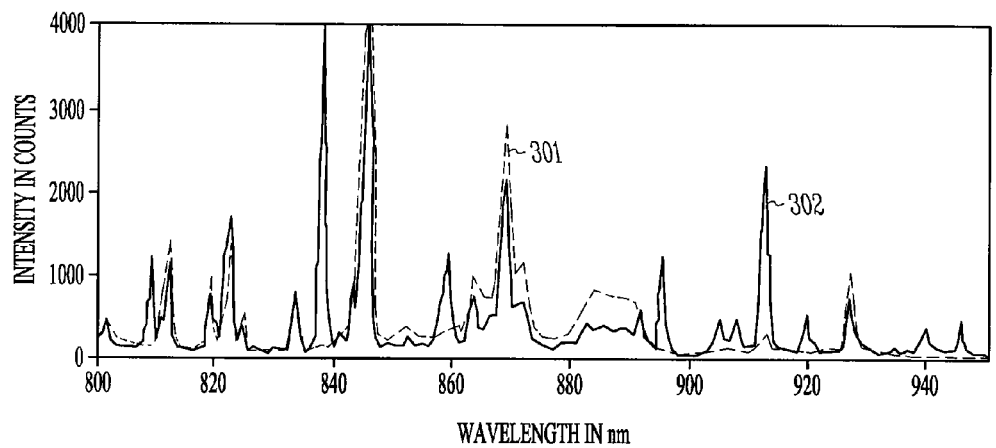
FIG. 4A shows two superimposed microdischarge detection spectra for air and trichloroethane analyte in air, respectively.
Figure 4B:
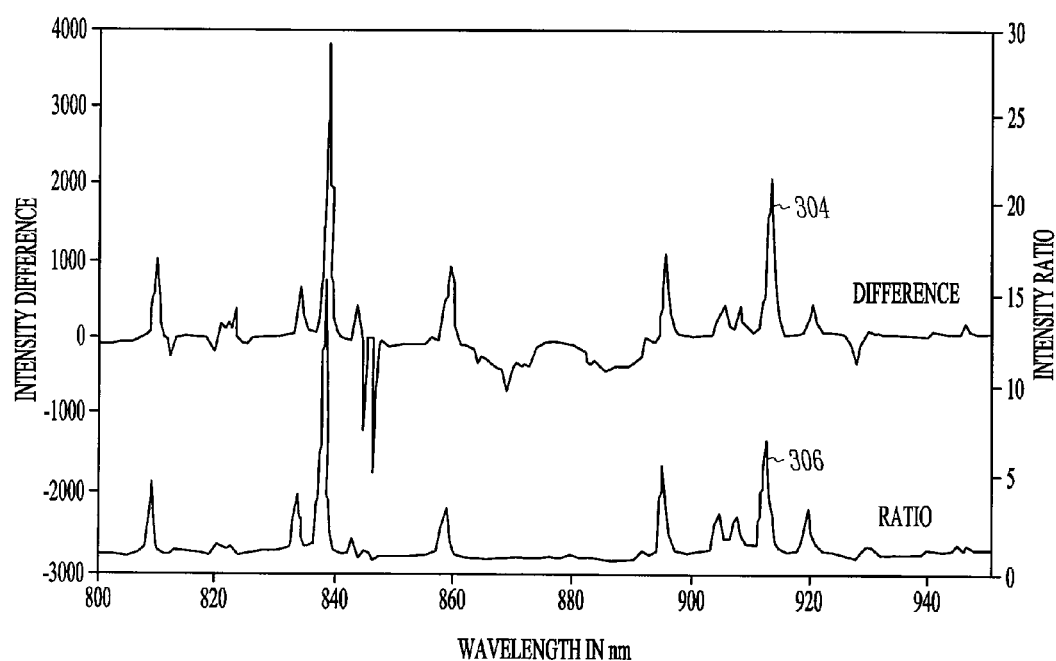
FIG. 4B shows the difference and ratio between the microdischarge detection spectra for air and trichloroethane analyte in air.

FIGS. 4A and 4B illustrate some of the benefits of the present invention. FIG. 4A shows an example of two superimposed MDD spectra (by Caviton, Inc.) in which one is the spectral signature of air (dotted line 301) and the other is the spectral signature of trichloroethane analyte in air (solid line 302). As shown, the net signature of interest (of the trichlorothane) is obscured by the air MDD emission spectrum. However, in FIG. 4B, it can be seen that, by forming either the difference (line 304) or the ratio (line 306) between those two signatures, the reference signal that is common to both is largely suppressed or eliminated. It can be seen from FIGS. 4A and 4B that, of the two approaches, the ratio signal 306 actually is cleaner. Particularly, the $N_2$ bands (from reference air) in the ratio plot 306 seem to be less affected by influences of certain analytes, such as $O_2$ and CI, than the $N_2$ bands in the difference plot 304.

The baseline of the ratio signal is at "1", rather than "0" (as it is for the difference signal 304). In some applications, instead of the straight ratio, the log-of-ratio may be more useful.

In order to further ensure accurate measurements, the temperature in the two MDDs should be as equal as possible. This can be accomplished by providing a suitably large thermal conductance of the MDD support substrate. Steps also should be taken to equalize any stray capacitances in the MDD's. This can be accomplished by carefully observing and achieving symmetries in the circuit layout of the MDDs (not shown in the figures) in order to assure that stray capacitances in the two MDDs generally will be equal.

Even with circuit symmetry, the two MDDs could have asymmetric outputs. Merely as an example, the two MDDs could age differently over time because they are exposed to different gasses, which might result in noise in the differential signal (i.e., such that the two MDDs would not have the same spectral output even when exposed to the same gas). Using the ratio of the two signals seems to provide better immunity to this type of noise than using the difference. However, in an even further variation of the invention that provides better immunity to this type of noise, the processor 140 or other circuitry can be adapted to correct for differences in the circuitry of the two MDDs. For instance, during final testing of the product prior to laboratory use (or even periodically during its useful life), the same sample gas, preferably at the same pressure, temperature, velocity, and time can be passed through the two MDDs and their outputs digitally recorded. Any differences between the two outputs can then be calculated and stored and later applied to (e.g., subtracted from) the differential measurement signals during use of the instrument. As an additional measure, efforts can be made to minimize aging differences by operating the two MDDs under the same conditions.

In an alternative embodiment, it is possible to use a single MDD rather than two MDDs. Particularly, a single MDD can be coupled to the output of the gas chromatograph, like MDD 128 in FIG. 1. The measurement system could have stored in it the signature spectral emission of the carrier gas (or carrier with the unseparated and non-pre-concentrated sample gas) as obtained during periods of time when no sample pulse is being eluted. The measurement system could then mathematically calculate the difference and/or ratio of the two measurements. However, this approach is less desirable because it increases the possibility that an emission of an analyte of interest may be overlooked because the so-created background emission may erroneously include one or more analyte peaks. It also cannot take into account variations in pressure, temperature, and flow rate over time or variations in the composition of the carrier gas over time.

The use of a differential MDD is especially advantageous when the recording time is short, as it is with eluting gas chromatograph peaks, which may conventionally be 1-10 seconds, but only 10-100 milliseconds with a micro gas chromatograph, like the aforementioned PHASED.

Advantages of the present invention include the fact that the differential output may enable the use of air as the carrier gas rather than helium or hydrogen in some experiments that might not have previously permitted the use of air due to its complex composition. Furthermore, the differential measurement signals, not only eliminates or minimizes the interference signals caused by the carrier gas, per se, but also compensates for errors caused as age modifies the outputs of the MDD's or as changes in the sample or carrier gas temperature, absolute pressure, flow, composition and/or driver voltage modify the baseline. The differential concept of the present invention also may lead to improved ionization and optical MDD outputs.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. A microdischarge detection system comprising:
   a first microdischarge detector generating a first measurement signal;
   a second microdischarge detector generating a second measurement signal; and
   a circuit coupled to receive said first and second measurement signals and produce an output signal that is one of a difference between said first and second measurement signals and a ratio between said first and second measurement signals,
   wherein said circuit produces an output signal that is a ratio between said first and second measurement signals.

2. The microdischarge detector system of claim 1 wherein said first and second measurement signals are spectral emission measurements.

3. The microdischarge detector system of claim 1 wherein said first and second measurement signals are electrical signals in the form of any one of impedances, voltages and currents across electrodes of said microdischarge detectors.

4. The microdischarge detector system of claim 1 wherein said first and second microdischarge detectors each comprise a pair of electrodes through which a current passes and wherein said first microdischarge detector generates a spectral emission measurement signal and at least one of a current, voltage, and impedance across electrodes of said first microdischarge detector and said second microdischarge detector generates a spectral emission measurement signal and at least one of a current, voltage, and impedance across electrodes of said second microdischarge detector and further wherein said circuit comprises a first circuit coupled to receive said spectral emission measurement signals and a second circuit coupled to receive said at least one of a current, voltage, and impedance measurement signals.

5. The microdischarge detection system of claim 4 further comprising:
   a measurement system coupled to receive the outputs of the first and second circuits.

6. A gas chromatograph system comprising:
   a gas chromatograph having a carrier gas carrying a pulse of sample gas through a capillary that adsorbs and desorbs gasses passing therethrough;
   a bypass path through which passes said carrier gas either without said sample gas pulse or with said sample gas pulse in an unseparated and diluted form;
   a first microdischarge detector comprising a pair of electrodes defining a gap through which a current is made to pass, said first microdischarge detector coupled to an outlet of said capillary to receive gas that has flowed through said capillary and pass it through said gap so as to cause said gas passing through said gap to emit electromagnetic radiation, and further comprising a detector system for detecting the spectrum of said emitted electromagnetic radiation to generate a first measurement signal of said spectrum;
   a second microdischarge detector comprising a pair of electrodes defining a gap through which a current is made to pass, said second microdischarge detector coupled to an outlet of said bypass path to receive gas that has flowed through said bypass path and pass it through said gap so as to cause said gas passing through said gap to emit electromagnetic radiation, and further comprising a detector system for detecting the spectrum of said emitted electromagnetic radiation to generate a second measurement signal of said spectrum;

a first differential circuit coupled to receive said first and second measurement signals and produce a differential spectral output signal; and a measurement system coupled to analyze said differential spectral output signal and determine physical properties of said sample gas pulse therefrom.

7. The gas chromatograph system of claim 6 further comprising:

a second differential circuit coupled to receive said currents through said electrodes of said first and second microdischarge detectors, respectively, and produce a differential current output signal; and wherein said measurement system is further coupled to analyze said differential current output signal and determine physical properties of said sample gas pulse therefrom.

8. The gas chromatograph system of claim 7 wherein a length and cross section of said bypass path is selected relative to said capillary such that a time delay of a gas through said capillary to said first microdischarge detector and a time delay of a gas through said bypass path to said second microdischarge detector are equal.

9. The gas chromatograph system of claim 7 wherein said first and second microdischarge detectors have chambers having cross sections selected so that a velocity of gas passing through said gap of said first microdischarge detector is equal to a velocity of gas passing through said gap of said second microdischarge detector.

10. The gas chromatograph system of claim 7
wherein the gas chromatograph system maintains equal gas temperatures in said first and second microdischarge detectors.

11. The gas chromatograph system of claim 7 wherein said first and second microdischarge detectors have outlet ports for releasing gas from said detectors after it has passed through said gaps, wherein said outlet ports of said first and second microdischarge detectors are coupled together.

12. The gas chromatograph of claim 7 wherein said first differential circuit produces a signal representative of the ratio between said first and second measurement signals.

13. A method of measuring physical phenomena using a microdischarge detector comprising the steps of:

obtaining a first measurement with a first microdischarge detector, said measurement including background noise;

obtaining a second measurement of said background noise with a second microdischarge detector; and generating a differential measurement signal of said first and second measurements, wherein said generating step comprises determining a ratio between said second measurement signal and said first measurement signal.

14. The method of claim 13 wherein said first and second measurements are spectral emission measurements.

15. The method of claim 13 wherein said first and second measurement signals are one of voltages, impedances and currents through electrodes of said microdischarge detectors.

16. A method of performing gas chromatography comprising the steps of:

passing a sample gas carried in a carrier gas through a gas chromatograph capillary and into a first microdischarge detector;

passing said carrier gas through a bypass conduit and into a second microdischarge detector;

obtaining an emission spectrum measurement with said first microdischarge detector, said measurement including background noise;

obtaining a second measurement of said background noise with said second microdischarge detector;

generating a differential measurement signal of said first and second measurements; and analyzing said differential measurement signal to detect physical properties of said sample gas.

17. The method of claim 16 wherein said microdischarge devices each comprise a pair of electrodes defining a gap therebetween through which a current is passed to form an electrical discharge across said gap, said method further comprising the steps of:

obtaining a measurement of one of current, voltage, and impedance across said electrode pair of said first microdischarge detector;

obtaining a measurement of one of current, voltage, and impedance across said electrode pair of said second microdischarge detector;

generating a differential measurement signal of said first and second current measurements; and analyzing said differential current measurement signal to detect physical properties of said sample gas.

18. The method of claim 17 wherein a time delay for gas to pass through said gas chromatograph to said gap of said first microdischarge detector is equal to a time delay through said bypass conduit to said gap of said second microdischarge detector.

19. The method of claim 17 wherein a velocity of gas passing through said gap of said first microdischarge detector is equal to a velocity of gas passing through said gap of said second microdischarge detector.

20. The method of claim 17 wherein temperatures of said gas in said first and second microdischarge detectors are equal.

21. The method of claim 17 wherein a pressure of gas in said first microdischarge detector is equal to a pressure of gas in said second microdischarge detector.

22. The method of claim 16 wherein said generating step comprises obtaining a ratio between said second measurement signal and said first measurement signal.

23. The method of claim 16 wherein said second passing step comprises passing said carrier gas without said sample gas through said bypass conduit.

24. The method of claim 16 wherein said second passing steps comprises passing said carrier gas with said sample gas in an unseparated and diluted form through said bypass conduit.

* * * * *